United States Patent [19]

Khan et al.

[11] Patent Number: 5,413,797
[45] Date of Patent: May 9, 1995

[54] CONTROLLED RELEASE ACTH CONTAINING MICROSPHERES

[75] Inventors: M. Amin Khan, Burlington; Howard Bernstein, Cambridge, both of Mass.

[73] Assignee: Alkermes Controlled Therapeutics, Inc., Cambridge, Mass.

[21] Appl. No.: 268,715

[22] Filed: Jun. 30, 1994

Related U.S. Application Data

[63] Continuation of Ser. No. 849,754, Mar. 12, 1992, abandoned.

[51] Int. Cl.$^6$ .................... A61K 9/52; A61K 37/40; A61K 9/50
[52] U.S. Cl. .................... 424/489; 424/422; 424/423; 424/424; 424/426; 424/486; 424/434; 514/769; 514/772; 514/772.3; 514/805; 514/963
[58] Field of Search ............... 424/422, 423, 424, 426, 424/486, 489, 434; 514/805

[56] References Cited

U.S. PATENT DOCUMENTS

| | | | |
|---|---|---|---|
| 3,523,906 | 8/1970 | Hove et al. | 252/316 |
| 3,691,090 | 12/1972 | Kitajima et al. | 252/316 |
| 3,737,337 | 6/1973 | Hildegard et al. | 117/100 |
| 3,891,570 | 6/1975 | Fukushima et al. | 252/316 |
| 4,389,330 | 6/1983 | Tice et al. | 427/213.36 |
| 4,391,797 | 7/1983 | Folkman et al. | 424/19 |
| 4,530,840 | 7/1985 | Tice et al. | 514/180 |
| 4,542,025 | 9/1985 | Tice et al. | 424/78 |
| 4,675,800 | 6/1987 | Seki et al. | 363/68 |
| 4,767,628 | 8/1988 | Hutchinson | 424/426 |
| 4,835,139 | 5/1989 | Tice et al. | 514/15 |
| 4,891,225 | 1/1990 | Langer et al. | 424/428 |
| 4,897,268 | 1/1990 | Tice et al. | 424/455 |
| 4,906,474 | 3/1990 | Langer et al. | 424/428 |
| 4,962,091 | 10/1990 | Eppstein et al. | 424/85.6 |
| 5,019,400 | 5/1991 | Gombotz et al. | 424/497 |

FOREIGN PATENT DOCUMENTS

| | | |
|---|---|---|
| 0058481 | 8/1982 | European Pat. Off. |
| 2620621 | 3/1989 | France |

OTHER PUBLICATIONS

Benita, S., et al., "Characterization of drug-loaded poly(d,1-lactide) microspheres," 73 *J. Pharm. Sci.* 1721-1724 (Dec. 1984).

Sato, T., et al., "Porous biodegradable microspheres for controlled dry delivery. I. Assessment of processing conditions and solvent removal techniques," 5 *Pharmaceut. Res.* 21-30 (1988).

*Primary Examiner*—Thurman K. Page
*Assistant Examiner*—James M. Spear
*Attorney, Agent, or Firm*—Hamilton, Brook, Smith & Reynolds

[57] ABSTRACT

ACTH polymeric controlled release systems are described wherein the ACTH retains good biological activity and is released over an extended period of time following administration by injection. In the preferred embodiment, the ACTH polymeric microspheres are made using very cold temperatures to freeze the polymer-ACTH mixtures into polymeric microspheres with very high retention of biological activity and material. Sustained release of biologically active ACTH is achieved when the microspheres are tested in vitro, extending over a period of greater than one day to several months. Altered release can be achieved by inclusion of degradation modifiers, pore forming agents, and stabilizers of the ACTH.

12 Claims, 3 Drawing Sheets

CONTROLLED RELEASE ACTH CONTAINING MICROSPHERES

This application is a continuation of 07/849,754, filed Mar. 12, 1992, now abandoned.

BACKGROUND OF THE INVENTION

This invention generally relates to polymeric microspheres for controlled release of ACTH.

Adrenocorticotropic hormone (ACTH) is a polypeptide secreted by the anterior pituitary gland. The polypeptide contains 39 amino acids and has a molecular weight of about 4500 Daltons. ACTH is extracted from the pituitary of mammals, especially pigs, for clinical use. The activity of ACTH is defined by a USP assay in hypophysectomized rats.

ACTH stimulates the adrenal cortex to synthesize and secrete adrenocortical hormones including cortisol, corticosterone, several weakly androgenic steroids, and, to a very limited extent, aldosterone. Under normal circumstances, endogenous release of ACTH is stimulated by corticotropin releasing factor (CRF) which is secreted by the hypothalamus. Exogenously administered ACTH produces all of the pharmacological effects usually produced by endogenous ACTH.

ACTH is utilized for its anti-inflammatory and immunosuppressant properties. In particular, it has been used for the following indications: 1) acute exacerbations of Multiple Sclerosis, 2) acute exacerbations of rheumatic disorders such as Rheumatoid Arthritis and Psoriatic Arthritis, 3) acute episodes of Ulcerative Colitis, 4) Infantile spasms and 5) acute bouts of Systemic Lupus Erythematous. Currently, for clinical purposes, ACTH is available as Corticotropin TM for injection, repository Corticotropin TM injection (containing partially hydrolyzed gelatin) and Corticotropin TM zinc hydroxide suspension.

Corticotropin injection is rapidly absorbed following IM or SQ injection, whereas after injection of corticotropin zinc hydroxide suspension or repository corticotropin injection, the drug is absorbed over a period of 4–10 hours, and plasma levels return to baseline after 24 hours.

ACTH is generally administered once or twice a day for up to 7–21 days, necessitating frequent IV or IM or SQ injections. The advantages of a controlled release formulation for ACTH include increased patient compliance and acceptance by reducing the number of injections, increased therapeutic benefit by eliminating the peak and valley changes in blood levels, and potentially lowering the total administered amount of drug by reducing peaks and valleys.

One means for controlling blood levels of a compound is to administer it in the form of a polymeric matrix that releases compound as a function of polymer degradation and/or drug diffusion. A variety of biodegradable and non-biodegradable polymers have been used for such applications, including polyesters such as poly(lactide-co-glycolide)s, polyanhydrides, polyorthoesters, and ethylenevinyl acetate polymers. In general, release is controlled by selection of the appropriate polymer, encapsulation conditions, and drug loading and excipients.

Examples of these polymeric systems are described in U.S. Pat. No. 4,891,225 to Langer and U.S. Pat. No. 4,906,474 to Langer (polyanhydrides), U.S. Pat. No. 4,391,797 to Folkman, et al., (ethylenevinyl acetate polymers), U.S. Pat. No. 4,767,628 to Hutchinson (polylactide, polylactide-co-glycolide acid), and U.S. Pat. No. 4,530,840 to Tice, et al. (polylactide, polyglycolide, and copolymers).

However, controlled release at the desired rate and over the desired period is difficult to achieve. Moreover, the conditions used to encapsulate the drug must not result in degradation of the drug to be delivered nor must the drug react with the polymeric matrix so as to inactivate or bind the drug. As important in a clinical situation, the delivery means must be cost effective to produce, stable to storage, and administrable using standard methodology.

It is therefore an object of the present invention to provide a method for making microspheres containing ACTH with very little loss of activity or material, and the resulting ACTH containing microspheres.

It is a further object of the present invention to provide a method for making microspheres formed from a broad range of polymers which contain active ACTH releasable in a controlled fashion, and the microspheres produced by such a process.

SUMMARY OF THE INVENTION

ACTH polymeric controlled release systems are described wherein the ACTH retains good biological activity and is released over an extended period of time following administration. In the preferred embodiment, the ACTH polymeric microspheres are made using very cold temperatures to freeze the polymer-ACTH mixtures into polymeric microspheres with very high retention of biological activity and material. Polymer, preferably a poly(lactide), is dissolved in a solvent such as methylene chloride together with powdered ACTH. The polymer/ACTH mixture is atomized into a vessel containing a frozen non-solvent such as ethanol, overlayed with a liquified gas such as nitrogen, at a temperature below the freezing point of the polymer/active agent solution or suspension. The atomized particles freeze into microspheres upon contacting the cold liquified gas, then sink onto the frozen non-solvent layer. The frozen non-solvent is then thawed. As the non-solvent thaws, the microspheres are still frozen and sink into the liquid non-solvent. The solvent in the microspheres also thaws and is slowly extracted into the non-solvent, resulting in hardened microspheres containing the ACTH.

Sustained release of biologically active ACTH is achieved when the microspheres are tested in vitro or in vivo, extending over a period of one day up to three months. Altered release can be achieved by inclusion of polymer degradation modifiers, pore forming agents, and stabilizers of the ACTH.

DETAILED DESCRIPTION OF THE INVENTION

Figure 1:
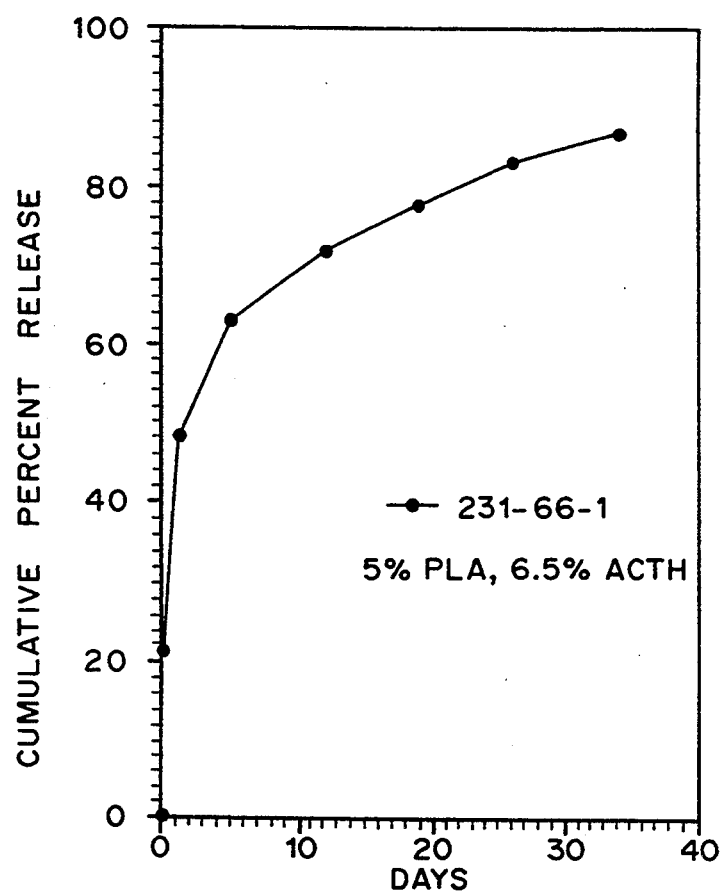
FIG. 1 is a graph of ACTH release (cumulative percent release) over time (days) from 5% L-PLA microspheres containing 6.5% ACTH.

ACTH containing microspheres are made by incorporating the ACTH into a biocompatible polymeric microsphere, up to approximately 50% w/w, wherein the microsphere containing the ACTH is characterized by sustained controlled release of the ACTH over a period of at least 24 hours up to a period of one to two months. In the preferred embodiment, the polymer is biodegradable, most preferably by hydrolysis, the microspheres have a diameter of less than one hundred eighty microns, most preferably less than seventy microns, and are suitable for administration by injection subcutaneously or intramuscularly (a size suitable for injection through a 23-gauge needle would be less than 180 µm in diameter), and the microspheres contain from 0.01% by weight up to approximately 50% by weight ACTH.

As used herein, "microsphere" is used to mean solid spheres formed of polymer having ACTH dispersed throughout, as well as microparticulates and microcapsules, unless otherwise noted. Microparticulates are specifically referred to when describing irregularly shaped polymer or polymer-drug particles. Microcapsules are spherical shaped polymer devices having a non-polymer core or a core of a different polymer than the outer shell.

As used herein, "sustained" or "extended" release of the ACTH can be continuous or discontinuous, linear or non-linear. This can be accomplished using one or more types of polymer compositions, drug loadings, selections of excipients or degradation enhancers, or other modifications, administered alone, in combination or sequentially to produce the desired effect.

ACTH is available in the form of Corticotropin TM for injection (Parke Davis, Rorer 25–40 Units/ml), repository Corticotropin TM injection (containing partially hydrolyzed gelatin, Rorer, 40–80 Units/ml) and Corticotropin TM zinc hydroxide suspension (Organon, 40 Units/ml). It is available in lyophilized form from Diosynth, Chicago, Ill.

Methods for Incorporation of ACTH into Microspheres.

A variety of techniques are known by which active agents can be incorporated into polymeric microspheres.

Spray Drying

In spray drying, the polymer and ACTH are mixed together in a solvent for the polymer, then the solvent is evaporated by spraying the solution, leaving polymeric droplets containing the active agent. Spray drying is reviewed in detail by K. Masters in "Spray Drying Handbook" (John Wiley & Sons, New York 1984); and Patrick B. Deasy in "Microencapsulation and Related Drug Processes" (Marcel Dekker, Inc., New York 1984), the teachings of which are incorporated herein. Spray drying is not preferred since it may result in some loss of activity due to the heat generated in the process as well as in loss of considerable amounts of the material due to sticking of the polymer to the large surface area on the sides of the chamber.

Solvent Evaporation

Solvent evaporation techniques can be used to form microspheres. These techniques involve dissolving the polymer in an organic solvent which contains either dissolved or dispersed active agent. The polymer/active agent solution is then added to an agitated continuous phase which is usually aqueous. Emulsifiers are included in the aqueous phase to stabilize the oil-in-water emulsion. The organic solvent is then evaporated over a period of several hours or more, thereby depositing the polymer around the core material. Solvent can be removed from the microspheres in a single step, as described in U.S. Pat. No. 3,737,337 and U.S. Pat. No. 3,523,906, or in U.S. Pat. No. 3,691,090 (under reduced pressure), or by the application of heat, as shown in U.S. Pat. No. 3,891,570. A two-step technique is described in U.S. Pat. No. 4,389,330. Freeze drying has also been used to remove the solvent from microspheres, as reported by Sato, et al, in "Porous Biodegradable Microspheres for Controlled Drug Delivery. I. Assessment of Processing Conditions and Solvent Removal Techniques," *Pharmaceutical Research* 5, 21–30 (1988). The teachings of these methods are incorporated herein.

Solvent evaporation works reasonably well but is not preferred since the amount of incorporated material is usually lower than the theoretical values due to loss of drug to the aqueous phase, as reported by Benita, et al., in "Characterization of Drug Loaded Poly(d,l-lactide) Microspheres," *J. Pharm. Sci.* 73, 1721–1724 (1984).

Phase Separation

Phase separation techniques can also be used to form microspheres. These techniques involve the formation of a water-in-oil emulsion or oil in water emulsion. The polymer is precipitated from the continuous phase onto the active agent by a change in temperature, pH, ionic strength or the addition of precipitants. For example, U.S. Pat. No. 4,675,800, et al., describes the formation of poly(lactic-co-glycolic) acid microspheres containing active proteins. The protein is first dissolved in the aqueous phase of a water-in-oil emulsion or dispersed as a solid in the polymer phase. Polymer is then precipitated around the aqueous droplets or drug particles by addition of a non-solvent for the polymer such as silicone oil. The final product, as with most phase separation techniques, is in the form of a microcapsule. Microcapsules contain a core material surrounded by a polymer membrane capsule. Microcapsules are not the preferred embodiment for delivery of ACTH, however, since the release kinetics of active agents from these devices can be difficult to control.

Although these phase separation techniques result in the formation of microspheres containing active agents, active agent is often lost during the solvent extraction process. In addition, as with spray drying, biologically active proteins may be denatured during the process.

Rapid Freezing, Solvent Extraction

The preferred method for making ACTH microspheres having the desired characteristics is described in U.S. Pat. No. 5,019,400 to Gombotz, et al, the teachings of which are incorporated herein.

There are two principal embodiments of the system for making microspheres: a combination liquified gas—frozen non-solvent system and a frozen non-solvent system.

Polymer and agent to be encapsulated in solution are atomized using an ultrasonic device into a liquified gas. The atomized particles freeze when they contact the liquified gas (liquid nitrogen), forming frozen spheres.

These sink to the surface of the frozen non-solvent (ethanol). The liquid gas is evaporated and the spheres begin to sink into the non-solvent as the non-solvent thaws. The solvent in the spheres is extracted into the non-solvent to form microspheres containing the agent to be encapsulated. Other non-solvents such as hexane are added to the non-solvent (ethanol) to increase the rate of solvent extraction from certain polymers, where appropriate, for example, when spheres are formed of polylactide-co-glycolide polymers.

The liquified gas can be liquid argon (−185.6° C.), liquid nitrogen (−195.8° C.), liquid oxygen (−182.9° C.) or any other gas that results in the immediate freezing of the atomized particles into frozen spheres. Oxygen is not preferred since it is explosive and may cause oxidation of the protein.

Alternatively, a cold non-solvent for the polymer can be substituted for the combination of liquified gas-frozen no-solvent, provided the temperature of the non-solvent is below the freezing temperature of the polymer/active agent solution.

In both embodiments, it is important that the polymer/active agent freeze immediately upon contacting the cold liquid, and then be slowly thawed and the polymer solvent extracted from the microspheres.

The thawing rate is dependent on the choice of solvents and non-solvents. It is important to select a solvent for the polymer having a higher melting point than the non-solvent for the polymer so that the non-solvent melts first, allowing the frozen microspheres to sink into the liquid where they later thaw. If a cold liquid non-solvent system for making the polymeric microspheres is used, the microspheres will sink immediately into the non-solvent. As the solvent in the microsphere thaws, it is extracted into the non-solvent. The solvent for the polymer and the non-solvent for the polymer must be miscible to allow extraction of the solvent from the microspheres. Table 1 shows some polymer/solvent/non-solvent systems that can be used in this process along with their melting points.

TABLE 1

Polymers and Appropriate Solvents and Non-Solvents Systems, with Solvent and Non-Solvent Melting Points °C.

| POLYMER | SOLVENT | NON-SOLVENT |
|---|---|---|
| Poly(lactide | Methylene Chloride (−95.1) | Ethanol (−114.5) |
|  | Chloroform (−63.5) | Methanol (−97.5) |
| Poly(lactide-co-glycolide acid) | Ethyl Acetate (−83.6) | Ethanol (−114.5) |
|  | Acetone (−95.4) | Ethyl ether (−116.3) |
|  | Methylene Chloride (−95.1) | Isopentane (−130) |
| Poly(caprolactone) | Methylene Chloride (−95.1) | Ethanol (−114.5) |
| Poly (vinyl alcohol) | Water (0) | Acetone (−95.4) |
| Ethylene-vinyl acetate | Methylene Chloride (−95.0) | Ethanol (−114.5) |

The polymer/active agent/solvent mixture can be sprayed into the cold liquid, either the liquified gas or the cold non-solvent, using a variety of devices which can be used to form small particles, including sonic nozzles, pressure nozzles, pneumatic nozzles and rotary atomizers.

A wide range of sizes of microspheres can be made by varying the droplet size, for example, by changing the nozzle diameter. If very large spheres are desired, the spheres can be extruded through a syringe directly into the cold liquid. Increasing the inherent viscosity of the polymer solution can also result in an increasing microspheres size. The size of the spheres produced by this process can range from greater than 1000 to 5 microns in diameter. A preferred size range for injectable microspheres is from 30 to 180 microns in diameter. The microspheres made by this technique are spherical in shape.

Selection of the Polymeric Matrix

Polymers that can be used to form the microspheres include bioerodible polymers such as poly(lactide), poly(lactide-co-glycolide), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolefins, and polyethylene oxide. Almost any type of polymer can be used provided the appropriate solvent and non-solvent are found which have the desired melting points. In general, a polymer solution is prepared containing between 1% polymer and 30% polymer, preferably 5–10% polymer.

In the preferred embodiment, a poly(lactide) is used. As used herein, this term includes polymers of lactic acid or lactide alone, copolymers of lactic acid and glycolic acid, copolymers of lactide and glycolide, mixtures of such polymers and copolymers, the lactic acid or lactide being either in racemic or optically pure form. It is most desirable to use polylactides in the range of molecular weight up to 100,000.

The release of the ACTH from these polymeric systems can occur by two different mechanisms. The drug can be released by diffusion through aqueous filled channels generated in the dosage form by the dissolution of the drug or by voids created by the removal of the polymer solvent during the original microencapsulation. The second mechanism is enhanced release due to the degradation of the polymer. With time the polymer begins to erode and generates increased porosity and microstructure within the device. This creates additional pathways for drug release.

The degradation of the polymers occurs by spontaneous hydrolysis of the ester linkages on the backbone. Thus the rate can be controlled by changing polymer properties influencing water uptake. These include the monomer ratio (lactide to glycolide), the use of L-Lactide as opposed to D/L Lactide, and the polymer molecular weight. These factors determine the hydrophilicity and crystallinity which ultimately govern the rate of water penetration. Hydrophilic excipients such as salts, carbohydrates and surfactants can also be incorporated to increase water penetration into the devices and thus accelerate the erosion of the polymer.

By altering the properties of the polymer and the properties of the dosage form, one can control the contribution of each of these release mechanisms and alter the release rate of ACTH. Slowly eroding polymers such as poly L-lactide or high molecular weight poly(lactide-co-glycolide) with low glycolide compositions will cause the release to become diffusion controlled. Increasing the glycolide composition and decreasing the molecular weight enhances both water uptake and the hydrolysis of the polymer and adds an erosion component to the release kinetics.

The release rate can also be controlled by varying the loading of ACTH within the microspheres. Increasing the loading will increase the network of interconnecting channels formed upon the dissolution of the drug and enhance the release of drug from the microspheres. The preferred range of ACTH loadings is in the range of 3-30% (w/w).

Polymer hydrolysis is accelerated at acidic or basic pH's and thus the inclusion of acidic or basic excipients can be used to modulate the polymer erosion rate. The excipients can be added as particulates, can be mixed with the incorporated ACTH or can be dissolved within the polymer.

Excipients can be also added to the ACTH to maintain its potency depending on the duration of release. Stabilizers include carbohydrates, amino acids, fatty acids, and surfactants and are known to those skilled in the art. In addition, excipients which modify the solubility of ACTH such as salts, complexing agents (albumin, protamine) can be used to control the release rate of the protein from the microspheres.

Additives to Alter Release Rate, Degradation Rate, Stability of ACTH

Stabilizers for the ACTH are based on ratio to the protein on a weight basis. Examples include carbohydrate such as sucrose, lactose, mannitol, dextran, and heparin, proteins such as albumin and protamine, amino acids such as arginine, glycine, and threonine surfactants such as Tween TM and Pluronic TM, salts such as calcium chloride and sodium phosphate, and lipids such as fatty acids, phospholipids, and bile salts.

The ratios are generally 1:10 to 4:1, carbohydrate to protein, amino acids to protein, protein stabilizer to protein, and salts to protein; 1:1000 to 1:20, surfactant to protein; and 1:20 to 4:1, lipids to protein.

Degradation enhancers are based on weight relative to the polymer weight. They can be added to the protein phase, added as a separate phase (i.e., as particulates) or can be codissolved in the polymer phase depending on the compound. In all cases the amount should be between 0.1 and thirty percent (w/w, polymer). Types of degradation enhancers include inorganic acids such as ammonium sulfate and ammonium chloride, organic acids such as citric acid, benzoic acids, heparin, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween TM and Pluronic TM.

Pore forming agents to add microstructure to the matrices (i.e., water soluble compounds such as inorganic salts and sugars). They are added as particulates. The range should be between one and thirty percent (w/w, polymer).

Administration of the Microspheres to a Patient.

An effective amount of the microspheres containing ACTH are administered to a patient by injection subcutaneously, intramuscularly, intraperitoneally, and intradermally, by administration to mucosal membranes (such as intranasally or by means of a suppository), or by in situ delivery to provide the desired dosage of ACTH, based on the known parameters for treatment with ACTH of the various medical conditions, such as acute exacerbations of Multiple Sclerosis, acute exacerbations of rheumatic disorders such as Rheumatoid Arthritis and Psoriatic Arthritis, acute episodes of Ulcerative Colitis, acute bouts of Systemic Lupus Erythematous, and Infantile Spasms.

The present invention is further described by the following non-limiting examples.

Example 1: Preparation of Poly(L-lactic Acid) Microspheres Containing ACTH 0.52 g of poly(L-lactide) (Resomer L104, Boehringer Ingelheim, German) was dissolved in 5.0 ml of methylene chloride. To this polymer solution was added 38 mg of lyophilized porcine ACTH powder (Diosynth, Chicago, Ill.) with particle sizes in the range of 2 to 10 microns and the solution was placed in a 10 ml gas tight syringe. A 200 ml amount of 100% ethanol was added to a round polypropylene container (17 cm diameter, 8 cm deep). This solution was frozen in liquid nitrogen and covered with 500 ml of liquid nitrogen. The polymer protein mixture was pumped from the syringe via a syringe pump at 2 ml/min, into an ultrasonic nozzle (Model, Sonics and Material, Danbury, Conn.) that was placed above the container of liquid nitrogen and frozen ethanol. The nozzle atomized the suspension into droplets which froze upon contact with the liquid nitrogen and formed microspheres which sank onto the frozen ethanol.

The container was placed at $-80°$ C. where the liquid nitrogen evaporated and the ethanol melted with time. As the ethanol thaws, the microspheres settle into the liquid where the methylene chloride is extracted. After 24 hours, an additional 200 ml of 100% ethanol prechilled to $-80°$ C. was added to the container. After three days, the slurry of microspheres and ethanol was filtered using a one micron Durapore TM membrane (Millipore, Bedford, Mass.). The filtered microspheres were then lyophilized. The dried microspheres were suspended in a phosphate buffered saline pH 7.4 containing 0.01% sodium azide and the release of ACTH was monitored. Sustained release of ACTH was achieved for at least 35 days, as shown in FIG. 1.

Example 2: Preparation of Poly(D/L-lactic Acid) Microspheres Containing ACTH and Excipient The procedure in Example 1 was repeated except for the following modifications: 0.5 g of poly D/L lactide (Resomer R104, Boehringer Ingelheim, Germany) was dissolved in 2.5 ml methylene chloride. To this polymer solution was added 66 mg of lyophilized porcine ACTH and 63 mg calcium carbonate (Spectrum Chemicals, Calif.) as an excipient.

Figure 2:
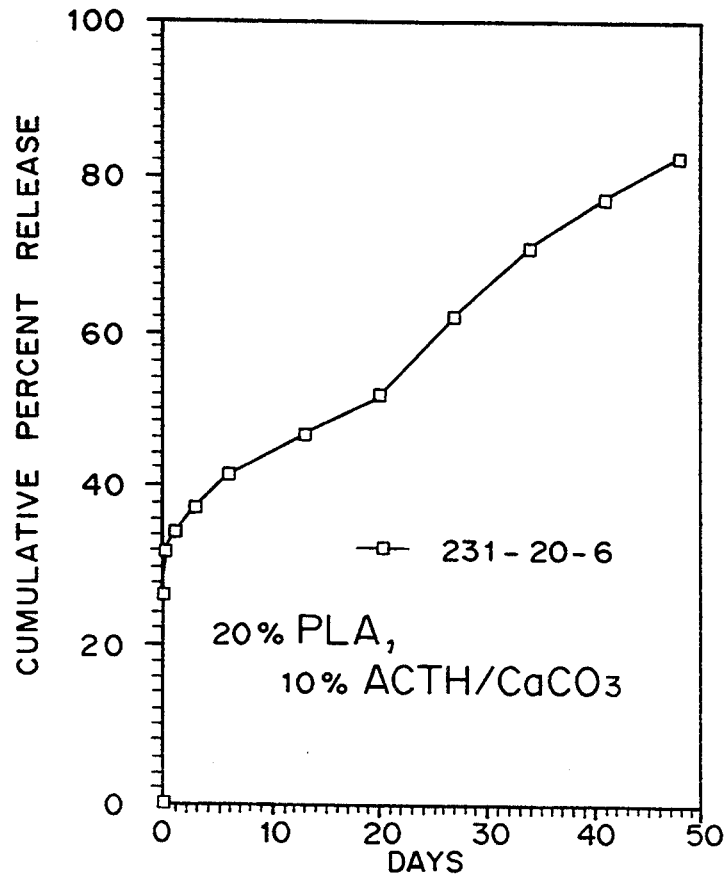
FIG. 2 is a graph of ACTH release (cumulative percent release) over time (days) from 20% DL-PLA microspheres containing 10% ACTH/CaCO$_3$.

Sustained release of ACTH was achieved for at least 45 days, as shown in FIG. 2.

Figure 3:
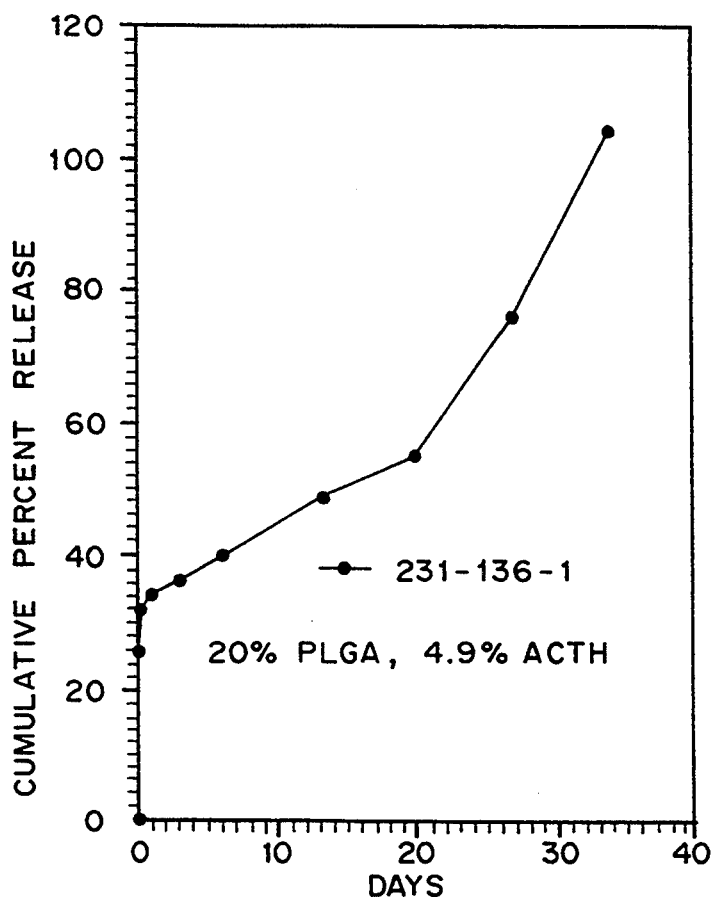
FIG. 3 is a graph of ACTH release (cumulative percent release) over time (days) from 20% PLGA microspheres containing 4.9% ACTH.

Example 3: Preparation of Poly(D/L-lactide Co-Glycolide) Microspheres Containing ACTH The procedure in Example 1 was repeated except for the following modifications: 0.51 g of poly(D/L lactide co-glycolide) (50:50) (inherent viscosity of 0.15 in hexafluoroisopropananol (Birmingham Polymers Inc., Birmingham, Ala.)) was dissolved in 2.2 ml of methylene chloride. To this polymer solution was added 29 mg of lyophilized porcine ACTH. Sustained release of ACTH was achieved for 35 days, as shown in FIG. 3.

Example 4: Preparation of Poly(L-lactide) Microspheres Containing ACTH

Figure 4:
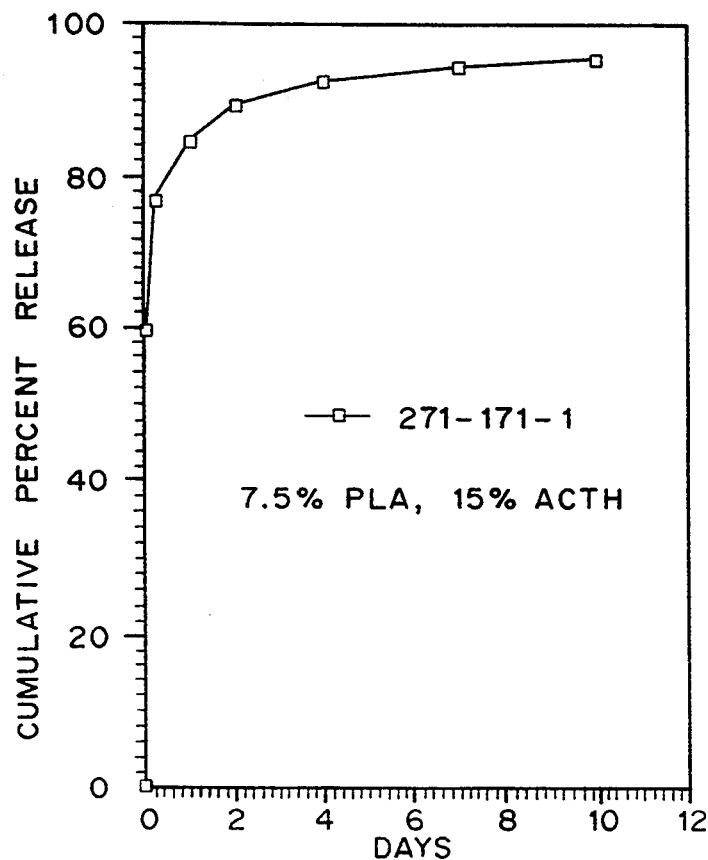
FIG. 4 is a graph of ACTH release (cumulative percent release) over time (days) from 7.5% L-PLA microspheres containing 15% ACTH.

The procedure in Example 1 was repeated except for the following modifications: 0.68 g of poly(L lactide (L104) was dissolved in 6.8 ml of methylene chloride. To this polymer solution was added 90 mg of lyophilized porcine ACTH. Sustained release of ACTH was achieved for ten days, as shown in FIG. 4.

Example 5: Preparation of Poly(L-lactide) Microspheres Containing ACTH

The procedure as in Example 1 was repeated except for the following modifications: 0.5 g of poly(L-lactide) (inherent viscosity 0.13 in chloroform) (Birmingham Polymers Inc., Birmingham, Ala.) was dissolved in 5.0 ml of methylene chloride. To this polymer solution was added 15 mg of lyophilized porcine ACTH. Four separate batches were prepared and pooled together after the lyophilization step.

Figure 5:
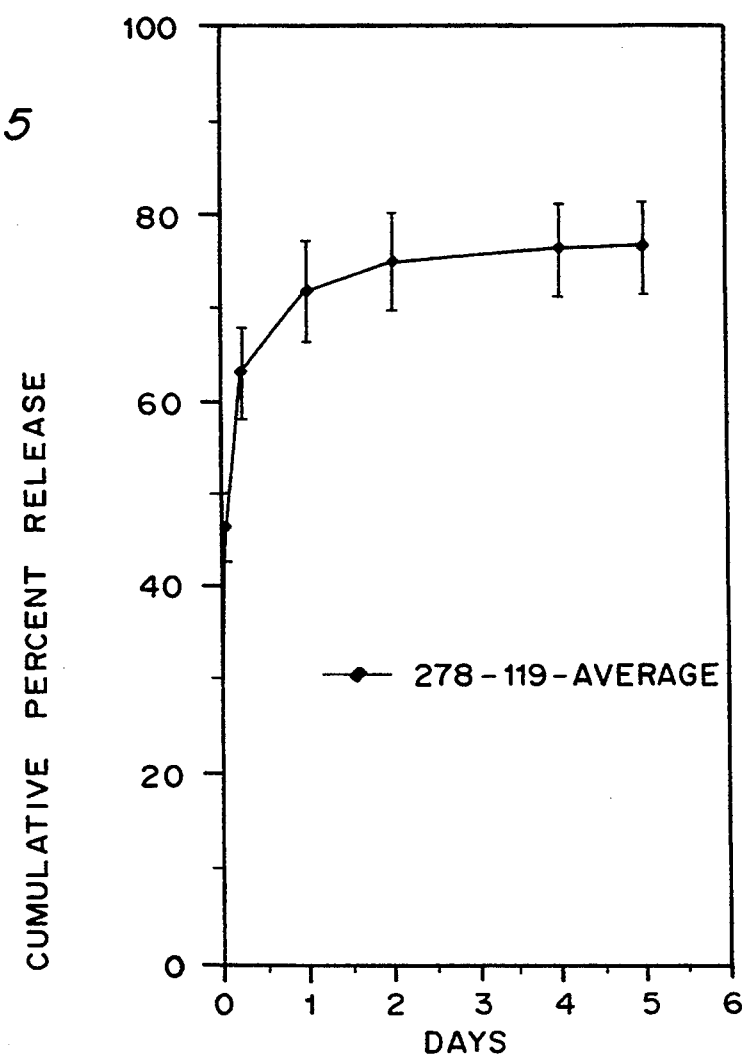
FIG. 5 is a graph of the cumulative percent release over time (days) of ACTH from L-PLA microspheres.

Sustained release of ACTH was achieved for five days from the pooled batch of microspheres, as shown in FIG. 5. ACTH was extracted out of the microspheres by dissolving the polymer in a mixture of methylene chloride and acetone. The recovered protein was tested for potency using the USP assay for ACTH. There was no significant change in potency as compared to the starting material.

Example 6: In vivo Pharmacodynamics of Release of ACTH from Microspheres Administered to Rats The pharmacodynamics of the microspheres made in example 5 were tested in vivo in rats and compared to the pharmacodynamics of an equivalent dose of soluble ACTH. Dexamethasone suppressed rats were used to completely suppress endogenous production of rat ACTH. Plasma corticosterone levels were followed with time as a measure of the biological activity of administered ACTH.

Figure 6:
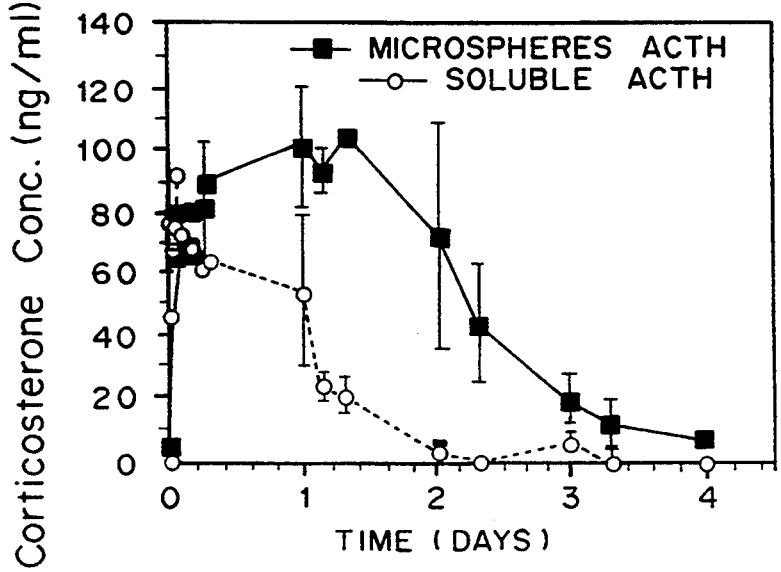
FIG. 6 is a graph of the corticosterone concentration (ng/ml) in rats administered either microencapsulated ACTH (dark squares) or soluble ACTH (open circles) over time (days).

Animals were injected subcutaneously with the ACTH microspheres or a solution of ACTH in water for injection no sooner than after four days of dexamethasone suppression. This assured achievement of stable plasma levels of corticosterone at or near zero ng/ml. Animals were anesthetized with methoxyflurane and blood samples were obtained from the tail vein prior to injection and at selected times up to three days post injection. Plasma was separated from the blood samples and assayed for corticosterone by RIA. Average corticosterone versus time curves for two microsphere ACTH and three soluble ACTH experiments, n which the dose of ACTH was roughly equivalent in all experiments, are presented in FIG. 6.

The observed elevation of corticosterone in ACTH microsphere injected animals lasted from about 1.5 to almost two times longer than that seen in ACTH solution injected animals given an equivalent dose, and the observed concentrations of corticosterone were greater in the microsphere injected animals over the course of the experiment than in the solution injected animals.

Modifications and variations of the present invention, a method for making microspheres, and products thereof, will be obvious to those skilled in the art from the foregoing detailed description of the invention. Such modifications and variations are intended to come within the scope of the appended claims.

We claim:

1. A polymeric microsphere having a diameter of less than 1000 microns, formed of a biocompatible polymer selected from the group consisting of poly(lactide), poly(lactide-co-glycolide), poly(caprolactone), polycarbonates, polyamides, polyanhydrides, polyamino acids, polyortho esters, polyacetals, polycyanoacrylates, degradable polyurethanes, polyacrylates, polymers of ethylene-vinyl acetate and other acyl substituted cellulose acetates, polysaccharides, non-erodible polyurethanes, polystyrenes, polyvinyl chloride, polyvinyl fluoride, poly(vinyl imidazole), chlorosulphonated polyolefins, polyethylene oxide, copolymers and mixtures thereof and an excipient modulating polymer erosion rate selected from the group consisting of inorganic acids, organic acids, inorganic bases, organic bases, and surfactants in an amount between 0.1 and thirty percent (w/w, polymer), containing adrenocorticotropic hormone (ACTH) in a concentration of between 0.1% and 50% by weight, wherein the microspheres release the ACTH under physiological conditions over a period of time greater than one day by diffusion and degradation of the polymeric matrix.

2. The microspheres of claim 1 wherein the polymer is a polylactide.

3. The microspheres of claim 1 wherein the diameter is less than 180 microns.

4. The microspheres of claim 1 further comprising an excipient selected from the group consisting of excipients stabilizing ACTH potency, and excipients modifying the solubility of ACTH.

5. The microspheres of claim 4 wherein the erosion rate modulating agent is a pore forming agent added to the polymer in particulate form in a concentration of between one and thirty percent (w/w, polymer).

6. The microspheres of claim 4 wherein the stabilizers are selected from the group consisting of carbohydrates, amino acids, proteins, lipids, salts, fatty acids, and surfactants.

7. The microspheres of claim 4 wherein the excipients which modify the solubility of ACTH are present in a concentration of between 0.1 and thirty percent (w/w, polymer) and are selected from the group consisting of salts, complexing agents, inorganic acids, organic acids, inorganic bases, organic bases, and surfactants.

8. A method for administering ACTH comprising administering a biocompatible polymeric microsphere containing between 0.1 and 50% ACTH and an excipient modulating polymer erosion rate, and having a diameter of less than one hundred eighty microns into a patient in need of treatment with ACTH, wherein the polymeric microsphere is formed of a biocompatible polymer selected from the group consisting of poly(lactide), poly(lactide-co-glycolide), poly(caprolactone), polycarbonates, polyamides, polyanhydrides, polyamino acids, polyortho esters, polyacetals, polycyanoacrylates, degradable polyurethanes, polyacrylates, polymers of ethylene-vinyl acetate and other acyl substituted cellulose acetates, polysaccharides, non-erodible polyurethanes, polystyrenes, polyvinyl chloride, polyvinyl fluoride, poly(vinyl imidazole), chlorosulphonated polyolefins, polyethylene oxide, copolymers, and mixtures thereof and an excipient modulating polymer erosion rate selected from the group consisting of inorganic acids, organic acids, inorganic bases, organic bases, and surfactants in an amount between 0.1 and thirty percent (w/w, polymer), wherein the ACTH is released over a period of time in excess of one day by diffusion and degradation of the polymeric matrix.

9. The method of claim 8 wherein the microspheres are administered by application to a mucosal membrane.

10. The method of claim 8 wherein the polymer is a polylactide.

11. The method of claim 8 wherein the diameter of the microspheres is less than 70 microns.

12. The method of claim 8 wherein the microspheres are administered by injection intramuscularly, subcutaneously, intraperitoneally, or intradermally.

* * * * *